US00PP24313P2

(12) United States Plant Patent
Zary

(10) Patent No.: US PP24,313 P2
(45) Date of Patent: Mar. 18, 2014

(54) SHRUB ROSE PLANT NAMED 'ZARSBSUN'

(50) Latin Name: *Rosa×hybrida*
Varietal Denomination: ZARSBSUN

(76) Inventor: Keith Zary, Troy, OH (US)

( * ) Notice: Subject to any disclaimer, the term of this patent is extended or adjusted under 35 U.S.C. 154(b) by 98 days.

(21) Appl. No.: 13/506,869

(22) Filed: May 22, 2012

Related U.S. Application Data

(60) Provisional application No. 61/571,574, filed on Jul. 1, 2011.

(51) Int. Cl.
*A01H 5/00* (2006.01)

(52) U.S. Cl.
USPC ..... Plt./104; Plt./101; Plt./102

(58) Field of Classification Search
USPC ..... Plt./101, 102, 104
See application file for complete search history.

*Primary Examiner* — Susan McCormick Ewoldt

(57) ABSTRACT

A new cultivar of *Rosa* named 'ZARSBSUN' that is distinguishable by compact growth habit which requires limited pruning, dark green and glossy foliage, and flowers which open with a faint coral blush and become soft yellow. The flowers of 'ZARSBSUN' are semi-double and very long lasting, holding their color even in hot weather. 'ZARSBSUN' exhibits vigorous growth on its own roots, shows high disease resistance and is hardy to USDA Zone 5. In combination these traits set 'ZARSBSUN' apart from all other existing varieties of *Rosa* known to the inventor.

2 Drawing Sheets

Genus: *ROSA*.
Species: ×hybrida.
Denomination: 'ZARSBSUN'.

BACKGROUND OF THE INVENTION

This application claims the benefit of priority under 35 U.S.C. 119(e) of U.S. Provisional Application No. 61/571,574 filed on Jul. 1, 2011 entitled *ROSA* plant named 'ZARSBSUN'.

This application is also co-pending with the inventor's variety of Shrub Rose plant named 'ZARSBJOH'.

The present invention relates to a new and distinct cultivar of *ROSA* or shrub rose grown as an ornamental plant for use in the garden and landscape. The new invention is known botanically as *ROSA×hybrida* and will be referred to hereinafter by the cultivar name 'ZARSBSUN'.

'ZARSBSUN' is a complex hybrid plant that is the product of a breeding program to create new and improved varieties of garden roses in all commercial classes.

'ZARSBSUN' was selected as a seedling that resulted from the controlled cross-pollination carried out by the inventor in a cultivated area of Somis, Calif., USA. The breeding began in 1985 by crossing an individual plant *Rosa×hybrida* 'SCRivluv' (unpatented) as the female parent and an individual of *Rosa×hybrida* (species, unpatented) as the male parent. Seed was collected from hips formed on the female parent and coded as 3971, then sown with the intention of making a selection from the seedlings that resulted.

'ZARSBSUN' was selected in 2005 based on the criteria of disease resistance combined with a free flowering and compact plant habit, good tolerance to cold, ease of propagation and vigorous growth on its own roots. Selection was conducted by the inventor, in Somis, Calif., USA. The unique traits that distinguish 'ZARSBSUN' from other varieties of *Rosa* known to the inventor are resistance to common rose diseases; rust, powdery mildew and black spot. Ease of propagation from softwood cuttings and vigorous growth on its own roots.

'ZARSBSUN' is distinguishable from the parents predominantly by flower and foliage amount and size. The flowers of 'SCRivluv' (unpatented) female parent have fewer petals, five petals per flower, whereas the flowers of 'ZARSBSUN' have 20 to 25 petals per flower. 'SCRivluv' (unpatented) is also a larger plant at 75 cm×50 cm, whereas 'ZARSBSUN' is smaller at 45 cm×30 cm in size.

The male parent (species, unpatented) has flowers of larger size, 10 cm on average and much larger leaves, 15 cm×10 cm. 'ZARSBSUN' has flowers of a smaller size, 5 cm and smaller leaves, 8 cm×5 cm.

'ZARSBSUN' exhibits a compact rounded habit, dark green glossy foliage, semi-double flowers that open as soft yellow with a faint coral blush. The plants of 'ZARSBSUN' exhibit a long flowering period, typically May to early November. Cultural conditions include full sun, regular water and rich well-draining potting soil. 'ZARSBSUN' is hardy to USDA Zone 5 and grows to 61 cm in height and 46 cm in width at maturity.

The variety of *Rosa* which is considered by the inventor to most closely resemble 'ZARSBSUN' is *Rosa* 'SCRivluv' (unpatented) female parent. 'SCRivluv' have fewer petals per flower, five versus 20 to 25 for 'ZARSBSUN'. 'SCRivluv' is a smaller, more compact habit than 'ZARSBSUN'.

The first asexual reproduction of 'ZARSBSUN' was conducted in 2005 in Somis, Calif., USA. The method of asexual propagation utilized was softwood cuttings. Since that time under careful observation, the distinguishing characteristics have been determined stable, uniform, and to be reproduced true to type in subsequent generations of asexual propagation.

SUMMARY OF THE INVENTION

The following traits have been repeatedly observed and represent the distinguishing characteristics of the new *Rosa* cultivar named 'ZARSBSUN'. These traits in combination distinguish 'ZARSBSUN' from all other existing varieties of *Rosa* known to the inventor. 'ZARSBSUN' has not been tested under all possible conditions and phenotypic differences may be observed with variations in environmental, climatic, and cultural conditions, however, without any variance in genotype.

1. 'ZARSBSUN' exhibits compact growth habit which requires limited pruning.
2. 'ZARSBSUN' exhibits dark green and glossy foliage.
3. 'ZARSBSUN' bears coral buds that open as soft yellow flowers with a faint coral blush.
4. The flowers of 'ZARSBSUN' are semi-double and very long lasting, holding their color even in hot weather.
5. 'ZARSBSUN' exhibits vigorous growth on its own roots.
6. Plants of 'ZARSBSUN' exhibit a long flowering period, typically May to early November.
7. After one growing season, plants of 'ZARBSUN' are 45 cm in height and 30 cm in width
8. At maturity, plants of 'ZARSBSUN' are 46 cm to 61 cm in height and 30 cm to 46 cm in width.
9. 'ZARSBSUN' shows high disease resistance.
10. 'ZARSBSUN' is hardy to USDA Zone 5.

BRIEF DESCRIPTION OF THE DRAWINGS

The accompanying color drawings labeled

The drawing labeled FIG. 1 depicts the entire plant in bloom.

The drawing labeled FIG. 2 depicts a close-up view of a flower.

Figure 1:
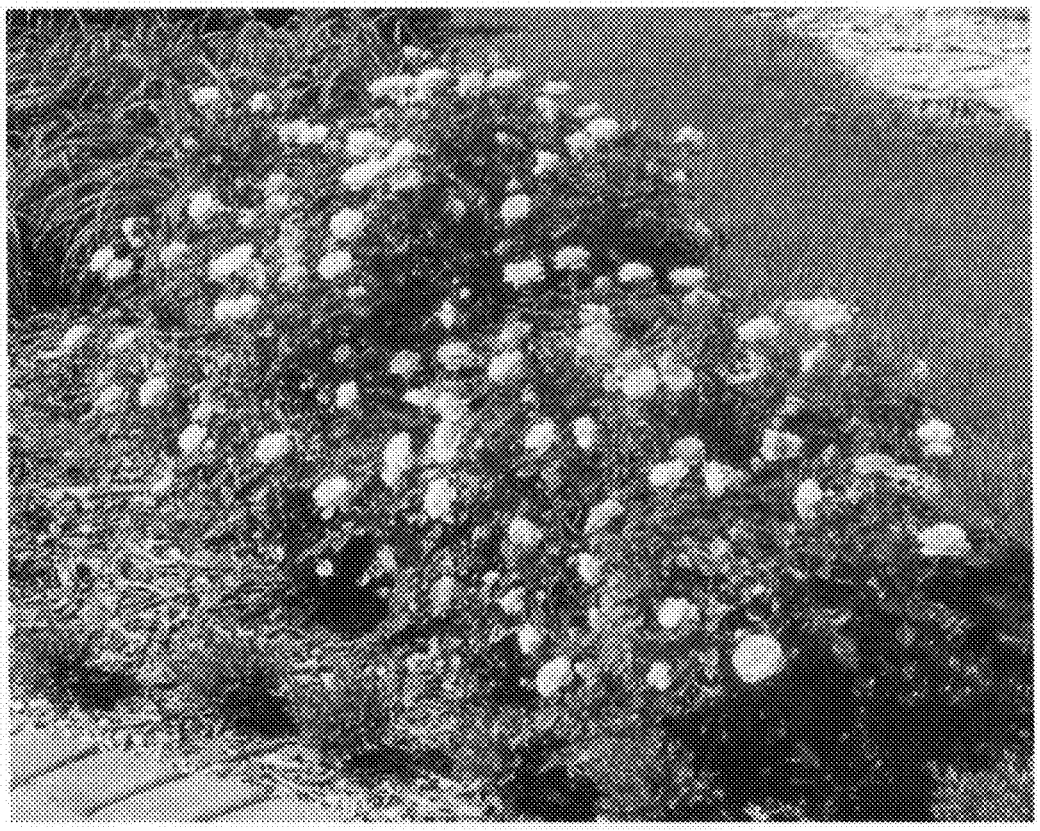
FIG. 1 and FIG. 2 illustrate the overall appearance of 'ZARSBSUN' showing the colors as true as is reasonably possible to obtain in colored reproductions of this type. Colors in the photographs may differ from the color values cited in the detailed botanical description, which accurately describes the actual colors of 'ZARSBSUN'.
Figure 2:
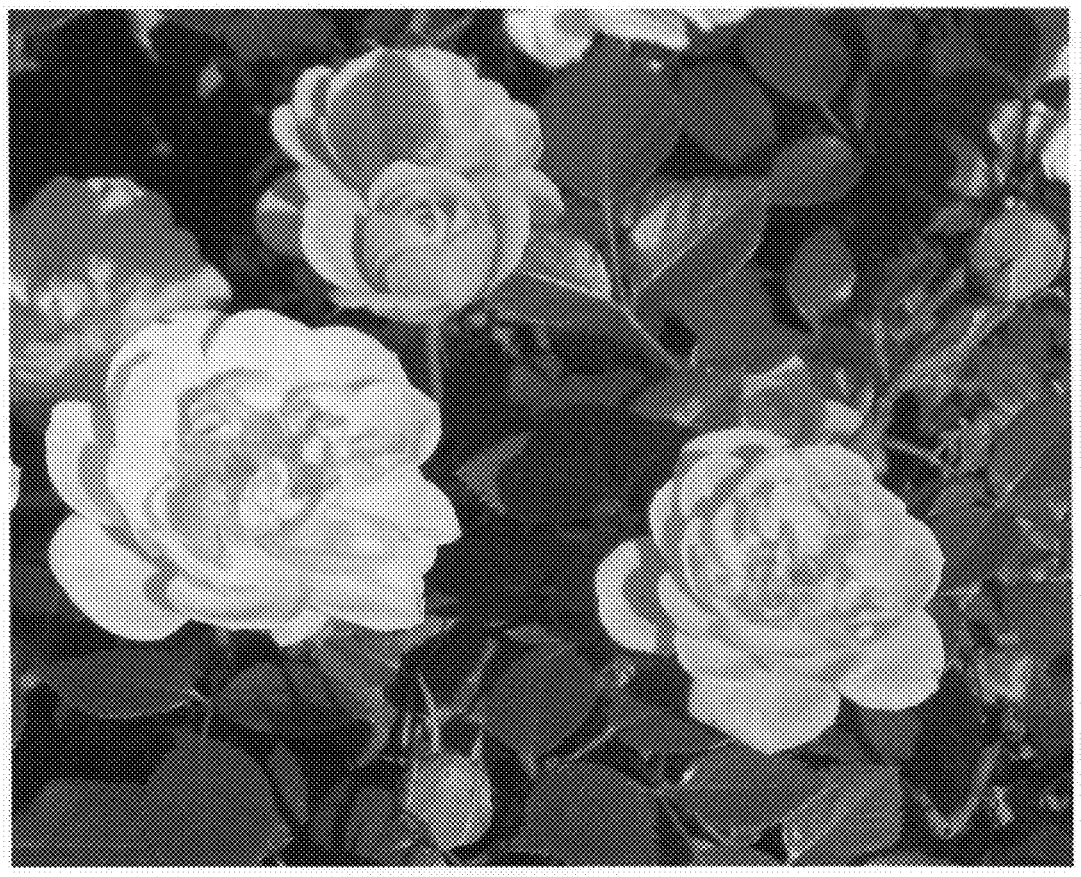

The drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Rosa* cultivar named 'ZARSBSUN'. Observations, measurements, values and comparisons were collected in Troy, Ohio from a 12 month old plant grown in the landscape. Color determinations were made in accordance with The 2001 Royal Horticultural Society Colour Chart from London England, except where general color terms of ordinary dictionary significance are used. Growing requirements are similar to the species.

Botanical classification: *Rosa×hybrida* 'ZARSBSUN'.
Family: Compositae.
Genus: *ROSA*.
Species: ×hybrida.
Denomination: 'ZARSBSUN'.
Common name: Rose.
Parentage: *Rosa×hybrida* 'ZARSBSUN' is a seedling that resulted from the controlled cross-pollination of the following parents:
  *Female parent.*—*Rosa×hybrida* 'SCRivluv' (unpatented).
  *Male parent.*—*Rosa* Unnamed yellow Floribunda (unpatented).
Propagation method: Asexual soft-wood cuttings.
Rooting system: Fine and fibrous.
Vigor: Vigorous growth on own roots.
Habit: Upright compact habit.
Use: For use in the garden and landscape.
Type: Perennial.
Dimensions: After one growing season, plants of 'ZARBSUN' are 45 cm in height and 30 cm in width. At maturity, plants of 'ZARSBSUN' are 46 cm to 61 cm in height and 30 cm to 46 cm in width.
Cultural requirements: Grow in full sun with regular water, and well-draining media.
Pest susceptibility: Susceptibility similar to the species.
Disease susceptibility: Resistant to common rose diseases: rust, powdery mildew and blackspot.
Hardiness: USDA Zone 5.
Stem:
  *Color, new wood.*—146D.
  *Color, old wood.*—146A.
  *Shape.*—Cylindrical.
  *Dimensions.*—Length: 30 cm-35 cm, diameter at base 1.5 cm, diameter below uppermost leaf 0.7 cm.
  *Bark surface.*—Smooth.
  *Internode length* (*average*).—12 cm.
Prickles:
  *Quantity.*—Ordinary, on main canes from base: 1 per cm of stem.
  *Quantity.*—Ordinary, on laterals from main canes: 1 per cm of stem.
  *Form.*—Straight.
  *Length.*—Ranges from 3 to 7 mm.
  *Color, when young.*—183D.
  *Color, when mature.*—N199B.
Small prickles:
  *Quantity.*—On main stalk: None observed.
  *Quantity.*—On lateral stalks: None observed.
Foliage:
  *Type.*—Evergreen.
  *Leaf arrangement.*—Alternate.
  *Leaf division.*—Pinnate.
  *Leaf dimensions* (*average*).—8 cm in length and 5 cm in width.
  *Leaf color* (*adaxial surface*).—137A.
  *Leaf color* (*abaxial surface*).—138B.
  *Leaflets.*—Leaflet number (average): 5. Size: 25 mm in length×20 mm in width. Shape: Obovate. Base shape: Oblique. Apex shape: Acuminate. Texture: Leathery, glossy. Edge: Serrated. Serrations: Single. Vein color: 147B. Venation pattern: Reticulate. Petiole color: 146D. Petiole rachis, Color: 146C. Petiole rachis, Underside: Smooth with occasional prickles. Auricles: None observed. Stipules: Present, fused to petiole; length 10 mm, shape serrated. Pest resistance: None observed (insects).
  *Inflorescence.*—
  *Inflorescence type.*—Terminal.
  *Form.*—When first open: High and centered.
  *Form.*—When mature: Flattens with age.
  *Inflorescence quantity.*—25 on average.
  *Dimensions of inflorescence* (*average*).—9.5 cm in diameter and 2.5 cm in depth.
  *Inflorescence shape.*—Radiate with center disk.
  *Blooming seasons.*—Spring through fall.

*Bud.*—Shape: Pointed ovoid, long. Dimensions (average): 17 mm in height and 9 mm in diameter. Color: When sepals first divide, bud color is 25D. Color: When half blown, the upper sides of the petals are 15D, lower sides are 12C. Sepals: Quantity: 5, shape spindly foliate with fine hairy and glandular margins. Of these, three are lightly appended and two are unappended. Sepals: Color: Upper surface: 138B. Sepals: Color: Lower surface: 138C. Sepal length: 11 mm-12 mm. Sepal width: 4 mm-5 mm. Sepal shape: Subulate. Surface texture: Hoary. Receptacles: Color: 138A. Receptacle shape: Funnel. Receptacle size: 7 mm in width and 5 mm in length. Receptacle surface: Smooth. Peduncle: Length short, average of 50 mm. Peduncle surface: Prickly. Peduncle: Color: 146C. Peduncle strength: Stiff.

*Blooms.*—Size: Small, average open diameter 50 mm. Borne: Singly. Stems: Strength: Strong. Average length is between 10 cm to 12 cm with a diameter of between 3 mm to 4 mm. Form: When first open: High and centered. Form: When mature: Bloom flattens with age. Petalage: Number of petals under normal conditions: Average of 25. Petalage Color (upper): 15D. Petalage Color (lower): 12C. Petalage Color (base): Small 2 mm×2 mm color spot of 2A. Discoloration: The general tonality at the end of the first to fourth day is little changed, general tonality at the end of the fifth day fades to 13D. Fragrance: Moderate, honeysuckle scent.

*Petals.*—Thickness: Thick, leathery. Surface texture: Smooth. Shape: Round to deltoid. Margin: Entire. Apex shape: Rounded. Base shape: Cuneate. Form: Flat to slightly cupped. Arrangement: Imbricated. Petaloids, Number: 2 to 5. Petaloid Color: 15D. Persistence: Petals drop off cleanly before drying. Lastingness: On the plant: Fair, about 5 to 6 days. Lastingness: As a cut flower: Fair, about 6 to 7 days.

*Reproductive organs.*—Stamens: Number: Average of 55 to 60. Length: 2 mm. Anthers: Length: 7 mm. Color: 13A. Arrangement: Regular around styles, mixed with occasional petaloids. Filaments: Color: 13A. Length: Average of 5 mm to 6 mm in length. Pollen: Color: 163C. Pistils: Number: Average of 15 to 20. Length: 3 mm. Styles: Color: 35B. Length: 2 mm. Stigmas: Color: 160C. Length: 1 mm.

*Hips.*—Hips have not been observed during repeated observations.

The invention claimed is:

1. A new and distinct cultivar of *Rosa* plant named 'ZARSBSUN' as described and illustrated herein.

* * * * *